United States Patent
Matsuda et al.

(10) Patent No.: US 8,568,886 B2
(45) Date of Patent: Oct. 29, 2013

(54) FLUORINE-CONTAINING COPOLYMER, PAPER PROCESSING AGENT, AND COATING FILM-FORMING AGENT FOR COSMETIC PREPARATION

(75) Inventors: Michio Matsuda, Osaka (JP); Tetsuya Uehara, Osaka (JP); Mitsuhiro Usugaya, Osaka (JP); Ikuo Yamamoto, Osaka (JP); Takashi Enomoto, Osaka (JP); Kayo Kusumi, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 337 days.

(21) Appl. No.: 12/935,554

(22) PCT Filed: Mar. 27, 2009

(86) PCT No.: PCT/JP2009/056289
§ 371 (c)(1),
(2), (4) Date: Sep. 29, 2010

(87) PCT Pub. No.: WO2009/123051
PCT Pub. Date: Oct. 8, 2009

(65) Prior Publication Data
US 2011/0027593 A1 Feb. 3, 2011

(30) Foreign Application Priority Data
Mar. 31, 2008 (JP) ................................. 2008-091168

(51) Int. Cl.
*B32B 27/10* (2006.01)
(52) U.S. Cl.
USPC ............................. 428/421; 526/245; 524/544
(58) Field of Classification Search
USPC ............................. 428/421; 526/245; 524/544
See application file for complete search history.

(56) References Cited

U.S. PATENT DOCUMENTS

| | | | |
|---|---|---|---|
| 3,654,244 A | 4/1972 | Pittman | |
| 3,920,614 A | 11/1975 | Kirimoto et al. | |
| 4,127,711 A | 11/1978 | Lore et al. | |
| 6,355,753 B1 * | 3/2002 | Yamana et al. | 526/292.3 |
| 6,472,019 B1 * | 10/2002 | Yamaguchi et al. | 427/354 |
| 7,485,688 B2 | 2/2009 | Maekawa et al. | |

FOREIGN PATENT DOCUMENTS

| | | | |
|---|---|---|---|
| FR | 2 255 321 A1 | | 7/1975 |
| JP | 04-068006 | * | 3/1992 |
| JP | 04-068006 A | | 3/1992 |
| JP | 2000-226419 | * | 8/2000 |
| JP | 2001-302732 | * | 10/2001 |
| JP | 2001-302732 A | | 10/2001 |
| JP | 2007-108512 | * | 4/2007 |
| JP | 2007-108512 A | | 4/2007 |
| WO | 2005/090423 A1 | | 9/2005 |
| WO | WO-2005/090423 A1 | * | 9/2005 |

OTHER PUBLICATIONS

Federal Register http://www.epa.gov/opptintr/pfoa/pfoafr.pdf, Apr. 16, 2003, 8 pages, vol. 68, No. 73.
EPA Environmental News for Release: Monday Apr. 14, 2003, EPA Intensifies Scientific Investigation of a Chemical Processing Aid, http://www.epa.gov/opptintr/pfoa/pfoaprs.pdf, 2 pages
EPA OPPT Fact Sheet, http://www.epa.gov/opptintr/pfoa/pfoafacts.pdf, Apr. 14, 2003.
"Preliminary Risk Assessment of the Developmental Toxicity Associated With Exposure to Perfluorooctanoic Acid and Its Salts", U.S. Environmental Protection Agency Office of Pollution Prevention and Toxics Risk Assessment Division, Apr. 10, 2003, 63 pages.

* cited by examiner

Primary Examiner — Peter D. Mulcahy
Assistant Examiner — Henry Hu
(74) Attorney, Agent, or Firm — Sughrue Mion, PLLC

(57) ABSTRACT

Disclosed is a fluorine-containing copolymer having sufficient stability in water, which is capable of providing paper with sufficient oil resistance. The fluorine-containing polymer contains, as essential components, (a) a fluorine-containing monomer represented by general formula (I) $CH_2=C(-X)-C(=O)-Y-[-(CH_2)_m-Z-]_p-(CH2)_n-Rf$ (wherein X represents a hydrogen atom; Y represents $-O-$ or $-NH-$; Z represents a direct bond, $-S-$ or $-SO_2-$; Rf represents a fluoroalkyl group having 1-6 carbon atoms; m is a number of 1-10; n is a number of 0-10; and p is 0 or 1) and (b) an alkoxy group-containing monomer represented by general formula (II) $CH_2=C(X')-C(=O)-O-(RO)_q-H$ (wherein X' represents a hydrogen atom or a methyl group; R represents an alkylene group having 2-4 carbon atoms wherein a part or all of hydrogen atoms may be substituted by a hydroxyl group; and q represent an integer of 1-50). The fluorine-containing polymer does not contain a monomer having an amino group.

10 Claims, No Drawings

FLUORINE-CONTAINING COPOLYMER, PAPER PROCESSING AGENT, AND COATING FILM-FORMING AGENT FOR COSMETIC PREPARATION

TECHNICAL FIELD

The present invention relates to a fluorine-containing copolymer and a treatment agent for paper comprising said fluorine-containing copolymer. Further, the present invention relates to a film-forming agent for cosmetics and a mold release agent comprising said fluorine-containing copolymer.

BACKGROUND ART

Hitherto, various fluorine-containing polymer compounds are proposed. The fluorine-containing polymer compounds have the advantageous effects of having properties excellent in heat resistance, oxidation resistance, weather resistance and the like. The fluorine-containing polymer compounds are used as, for example, a water- and oil-repellent agent and a soil release agent by utilizing the properties that the fluorine-containing polymer compounds have low free energy, i.e., difficulty in adherence.

Recently, with respect to compounds containing a Rf group having 8 carbon atoms prepared by telomerization, Federal Register (FR Vol. 68, No. 73/Apr. 16, 2003 [FRL-7303-8]) (http://www.epa.gov/opptintr/pfoa/pfoafr.pdf), EPA Environmental News for release Monday April, 2003 "EPA INTENSIFIES SCIENTIFIC INVESTIGATION OF A CHEMICAL PROCESSING AID" (http://www.epa.gov/opptintr/pfoa/pfoaprs.pdf), and EPA OPPT FACT SHEET Apr. 14, 2003 (http://www.epa.gov/opptintr/pfoa/pfoafacts.pdf) announced that a "telomer" may possibly metabolize or decompose to perfluorooctanoic acid (hereinafter abbreviated as "PFOA").

EPA (Environmental Protection Agency of USA) has announced that the EPA intensifies the scientific investigation on PFOA (cf. EPA Report "PRELIMINARY RISK ASSESSMENT OF THE DEVELOPMENTAL TOXICITY ASSOCIATED WITH EXPOSURE TO PERFLUOROOCTANOIC ACID AND ITS SALTS" (http://www.epa.gov/opptintr/pfoa/pfoara.pdf)).

U.S. Pat. No. 3,654,244 discloses that a fluorine-containing polymer comprising a fluorine-containing monomer and a water-soluble monomer is used as a soil release agent. We used this fluorine-containing polymer to treat with paper, but this polymer could not give enough oil-resistance to paper and could not be enough dispersed in water.

On the other hand, U.S. Pat. No. 4,127,711 discloses a fluorine-containing polymer comprising a fluorine-containing monomer, a water-soluble monomer and an amino monomer.

WO2005/090423 discloses that a fluorine-containing polymer comprising a fluorine-containing monomer, a water-soluble monomer and an amino monomer is used as a soil proofing agent for paper.

These fluorine-containing copolymers must contain the amino monomer as one component of a fluorine-free monomer and convert a part or all of the amino groups of the copolymer to amine salts or tertiary ammonium salts, in order to have good dispersibility in an aqueous medium and to improve storage stability. We used these fluorine-containing copolymers to treat paper, but enough oil-resistance was not provided.

Patent Document 1: U.S. Pat. No. 3,654,244
Patent Document 2: U.S. Pat. No. 4,127,711
Patent Document 3: WO2005/090423

DISCLOSURE OF THE INVENTION

Problems to be Solved by the Invention

An object of the invention is to provide a fluorine-containing copolymer which do not contain a monomer having amino group, has enough stability in an aqueous medium, and can give more enough oil-resistance to paper than a fluorine-containing copolymer containing a monomer having amino group, even if the polymer does not contain a monomer having amino group.

Means for Solving the Problems

The present invention provides a fluorine-containing polymer free from a monomer having an amino group, comprising (a) a fluorine-containing monomer of the general formula:

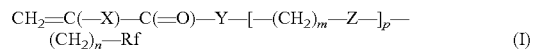

wherein X is a hydrogen atom, a methyl group, a fluorine atom, a chlorine atom, a bromine atom, a iodine atom, a $CFX^1X^2$ group (wherein $X^1$ and $X^2$ is a hydrogen atom, a fluorine atom or a chlorine atom), a cyano group, a linear or branched fluoroalkyl group having 1 to 20 carbon atoms, a substituted or unsubstituted benzyl group, or a substituted or unsubstituted phenyl group;
Y is —O— or —NH—;
Z is —S— or —$SO_2$—;
Rf is a fluoroalkyl group having 1 to 6 carbon atoms;
m is from 1 to 10, n is from 0 to 10, and p is 0 or 1, and
(b) an alkoxy group-containing monomer, which is a fluorine-free monomer and a compound [alkylene glycol (meth)acrylate] of the general formula:

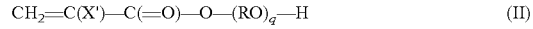

wherein X' is a hydrogen atom or a methyl group;
R is an alkylene group having 2 to 4 carbon atoms, in which a part or all of hydrogen atoms may be substituted with hydroxyl groups; and
q is an integer of 1-50.

Effects of the Invention

The fluorine-containing copolymer of the present invention has enough stability in the water and can give enough oil-resistance to paper, even if the copolymer does not contain the amino group.

MODES FOR CARRYING OUT THE INVENTION

Generally, the fluorine-containing copolymer of the present invention does not have repeating units derived from a monomer having an amino group.

The amino group is generally a group of the formula:

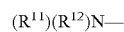

wherein $R^{11}$ and $R^{12}$ are, the same or different, a monovalent group (for example, a hydrogen atom). Generally, the monomer having an amino group has at least one carbon-carbon double bond in addition to the amino group.

The fluorine-containing monomer (a) is of the general formula:

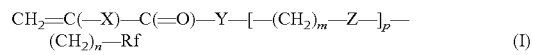

wherein X is a hydrogen atom, a methyl group, a linear or branched alkyl group having 1 to 21 carbon atoms, a fluorine atom, a chlorine atom, a bromine atom, a iodine atom, a $CFX^1X^2$ group (wherein $X^1$ and $X^2$ is a hydrogen atom, a fluorine atom or a chlorine atom), a cyano group, a linear or branched fluoroalkyl group having 1 to 21 carbon atoms, a substituted or unsubstituted benzyl group, or a substituted or unsubstituted phenyl group;

Y is —O— or —NH—;

Z is —S— or —$SO_2$—;

Rf is a fluoroalkyl group having 1 to 6 carbon atoms;

m is from 1 to 10, n is from 0 to 10, and p is 0 or 1.

In the general formula (I), p is preferably 0.

Preferred example of X is a hydrogen atom.

Generally, in the fluorine-containing monomer (a), the Rf group is a perfluoroalkyl group and/or a partially fluorinated fluoroalkyl group. The Rf group is preferably a perfluoroalkyl group. The number of carbon atoms in the Rf group is from 1 to 6. The number of carbon atoms in the Rf group may be 4, 5 or 6, particularly 6. Examples of the Rf group include —$CF_3$, —$CF_2CF_3$, —$CF_2CF_2CF_3$, —$CF(CF_3)_2$, —$CF_2CF_2CF_2CF_3$, —$CF_2CF(CF_3)_2$, —$C(CF_3)_3$, —$(CF_2)_4CF_3$, —$(CF_2)_2CF(CF_3)_2$, —$CF_2C(CF_3)_3$, —$CF(CF_3)CF_2CF_2CF_3$, and —$(CF_2)_5CF_3$.

m is 1 to 10, for example, 2 to 5, and n is 0 to 10, for example, 1 to 6, particularly 2 to 5.

The fluorine-containing monomer (a) may be used alone or in a mixture of at least two.

Examples of the fluorine-containing monomer (a) are as follows:

$CH_2$=C(—X)—C(=O)—O—$(CH_2)_m$—S—$(CH_2)_n$—Rf $CH_2$=C(—X)—C(=O)—O—$(CH_2)_m$—$SO_2$—$(CH_2)_n$—Rf $CH_2$=C(—X)—C(=O)—O—$(CH_2)_n$—Rf $CH_2$=C(—X)—C(=O)—NH—$(CH_2)_n$—Rf wherein X is a hydrogen atom, a methyl group, a fluorine atom, a chlorine atom, a bromine atom, a iodine atom, a $CFX^1X^2$ group (wherein $X^1$ and $X^2$ is a hydrogen atom, a fluorine atom or a chlorine atom), a cyano group, a linear or branched fluoroalkyl group having 1 to 20 carbon atoms, a substituted or unsubstituted benzyl group, or a substituted or unsubstituted phenyl group;

Rf is a fluoroalkyl group having 1 to 6 carbon atoms;

m is from 1 to 10, and n is from 0 to 10.

Examples of the component (a) are the followings, to which the present invention is not limited.

$CH_2$=C(—H)—C(=O)—O—$(CH_2)_2$—S—Rf
$CH_2$=C(—H)—C(=O)—O—$(CH_2)_2$—S—$(CH_2)_2$—Rf
$CH_2$=C(—H)—C(=O)—O—$(CH_2)_3$—$SO_2$—Rf
$CH_2$=C(—H)—C(=O)—O—$(CH_2)_2$—$SO_2$—$(CH_2)_2$—Rf
$CH_2$=C(—H)—C(=O)—O—$(CH_2)_2$—Rf
$CH_2$=C(—H)—C(=O)—NH—$(CH_2)_2$—Rf
$CH_2$=C(—H)—C(=O)—$OCH_2CH_2N(C_2H_5)SO_2$—Rf
$CH_2$=C(—H)—C(=O)—$OCH_2CH_2N(CH_3)SO_2$—Rf
$CH_2$=C(—H)—C(=O)—$OCH_2CH(OCOCH_3)CH_2$—Rf
$CH_2$=C(—$CH_3$)—C(=O)—O—$(CH_2)_2$—S—Rf
$CH_2$=C(—$CH_3$)—C(=O)—O—$(CH_2)_2$—S—$(CH_2)_2$—Rf
$CH_2$=C(—$CH_3$)—C(=O)—O—$(CH_2)_3$—$SO_2$—Rf
$CH_2$=C(—$CH_3$)—C(=O)—O—$(CH_2)_2$—$SO_2$—$(CH_2)_2$—Rf
$CH_2$=C(—$CH_3$)—C(=O)—O—$(CH_2)_2$—Rf
$CH_2$=C(—$CH_3$)—C(=O)—NH—$(CH_2)_2$—Rf
$CH_2$=C(—$CH_3$)—C(=O)—$OCH_2CH_2N(C_2H_5)SO_2$—Rf
$CH_2$=C(—$CH_3$)—C(=O)—$OCH_2CH_2N(CH_3)SO_2$—Rf
$CH_2$=C(—$CH_3$)—C(=O)—$OCH_2CH(OCOCH_3)CH_2$—Rf
$CH_2$=C(—F)—C(=O)—O—$(CH_2)_2$—S—Rf
$CH_2$=C(—F)—C(=O)—O—$(CH_2)_2$—S—$(CH_2)_2$—Rf
$CH_2$=C(—F)—C(=O)—O—$(CH_2)_2$—$SO_2$—Rf
$CH_2$=C(—F)—C(=O)—O—$(CH_2)_2$—$SO_2$—$(CH_2)_2$—Rf
$CH_2$=C(—F)—C(=O)—O—$(CH_2)_2$—Rf
$CH_2$=C(—F)—C(=O)—NH—$(CH_2)_2$—Rf
$CH_2$=C(—Cl)—C(=O)—O—$(CH_2)_2$—S—Rf
$CH_2$=C(—Cl)—C(=O)—O—$(CH_2)_2$—S—$(CH_2)_2$—Rf
$CH_2$=C(—Cl)—C(=O)—O—$(CH_2)_2$—$SO_2$—Rf
$CH_2$=C(—Cl)—C(=O)—O—$(CH_2)_2$—$SO_2$—$(CH_2)_2$—Rf
$CH_2$=C(—Cl)—C(=O)—O—$(CH_2)_2$—Rf
$CH_2$=C(—Cl)—C(=O)—NH—$(CH_2)_2$—Rf
$CH_2$=C(—$CF_3$)—C(=O)—O—$(CH_2)_2$—S—Rf
$CH_2$=C(—$CF_3$)—C(=O)—O—$(CH_2)_2$—S—$(CH_2)_2$—Rf
$CH_2$=C(—$CF_3$)—C(=O)—O—$(CH_2)_2$—$SO_2$—Rf
$CH_2$=C(—$CF_3$)—C(=O)—O—$(CH_2)_2$—$SO_2$—$(CH_2)_2$—Rf
$CH_2$=C(—$CF_3$)—C(=O)—O—$(CH_2)_2$—Rf
$CH_2$=C(—$CF_3$)—C(=O)—NH—$(CH_2)_2$—Rf
$CH_2$=C(—$CF_2H$)—C(=O)—O—$(CH_2)_2$—S—Rf
$CH_2$=C(—$CF_2H$)—C(=O)—O—$(CH_2)_2$—S—$(CH_2)_2$—Rf
$CH_2$=C(—$CF_2H$)—C(=O)—O—$(CH_2)_2$—$SO_2$—Rf
$CH_2$=C(—$CF_2H$)—C(=O)—O—$(CH_2)_2$—$SO_2$—$(CH_2)_2$—Rf
$CH_2$=C(—$CF_2H$)—C(=O)—O—$(CH_2)_2$—Rf
$CH_2$=C(—$CF_2H$)—C(=O)—NH—$(CH_2)_2$—Rf
$CH_2$=C(—CN)—C(=O)—O—$(CH_2)_2$—S—Rf
$CH_2$=C(—CN)—C(=O)—O—$(CH_2)_2$—S—$(CH_2)_2$—Rf
$CH_2$=C(—CN)—C(=O)—O—$(CH_2)_2$—$SO_2$—Rf
$CH_2$=C(—CN)—C(=O)—O—$(CH_2)_2$—$SO_2$—$(CH_2)_2$—Rf
$CH_2$=C(—CN)—C(=O)—O—$(CH_2)_2$—Rf
$CH_2$=C(—CN)—C(=O)—NH—$(CH_2)_2$—Rf
$CH_2$=C(—$CF_2CF_3$)—C(=O)—O—$(CH_2)_2$—S—Rf
$CH_2$=C(—$CF_2CF_3$)—C(=O)—O—$(CH_2)_2$—S—$(CH_2)_2$—Rf
$CH_2$=C(—$CF_2CF_3$)—C(=O)—O—$(CH_2)_2$—$SO_2$—Rf
$CH_2$=C(—$CF_2CF_3$)—C(=O)—O—$(CH_2)_2$—$SO_2$—$(CH_2)_2$—Rf
$CH_2$=C(—$CF_2CF_3$)—C(=O)—O—$(CH_2)_2$—Rf
$CH_2$=C(—$CF_2CF_3$)—C(=O)—NH—$(CH_2)_2$—Rf
$CH_2$=C(—F)—C(=O)—O—$(CH_2)_3$—S—Rf
$CH_2$=C(—F)—C(=O)—O—$(CH_2)_3$—S—$(CH_2)_2$—Rf
$CH_2$=C(—F)—C(=O)—O—$(CH_2)_3$—$SO_2$—Rf
$CH_2$=C(—F)—C(=O)—O—$(CH_2)_3$—$SO_2$—$(CH_2)_2$—Rf
$CH_2$=C(—F)—C(=O)—O—$(CH_2)_3$—Rf
$CH_2$=C(—F)—C(=O)—NH—$(CH_2)_3$—Rf
$CH_2$=C(—Cl)—C(=O)—O—$(CH_2)_3$—S—Rf
$CH_2$=C(—Cl)—C(=O)—O—$(CH_2)_3$—S—$(CH_2)_2$—Rf
$CH_2$=C(—Cl)—C(=O)—O—$(CH_2)_3$—$SO_2$—Rf
$CH_2$=C(—Cl)—C(=O)—O—$(CH_2)_3$—$SO_2$—$(CH_2)_2$—Rf
$CH_2$=C(—$CF_3$)—C(=O)—O—$(CH_2)_3$—S—Rf

CH₂=C(—CF₃)—C(=O)—O—(CH₂)₃—S—(CH₂)₂—Rf
CH₂=C(—CF₃)—C(=O)—O—(CH₂)₃—SO₂—Rf
CH₂=C(—CF₃)—C(=O)—O—(CH₂)₃—SO₂—(CH₂)₂—Rf
CH₂=C(—CF₂H)—C(=O)—O—(CH₂)₃—S—Rf
CH₂=C(—CF₂H)—C(=O)—O—(CH₂)₃—S—(CH₂)₂—Rf
CH₂=C(—CF₂H)—C(=O)—O—(CH₂)₃—SO₂—Rf
CH₂=C(—CF₂H)—C(=O)—O—(CH₂)₃—SO₂—(CH₂)₂—Rf
CH₂=C(—CN)—C(=O)—O—(CH₂)₃—S—Rf
CH₂=C(—CN)—C(=O)—O—(CH₂)₃—S—(CH₂)₂—Rf
CH₂=C(—CN)—C(=O)—O—(CH₂)₃—SO₂—Rf
CH₂=C(—CN)—C(=O)—O—(CH₂)₃—SO₂—(CH₂)₂—Rf
CH₂=C(—CF₂CF₃)—C(=O)—O—(CH₂)₃—S—Rf
CH₂=C(—CF₂CF₃)—C(=O)—O—(CH₂)₃—S—(CH₂)₂—Rf
CH₂=C(—CF₂CF₃)—C(=O)—O—(CH₂)₃—SO₂—Rf
CH₂=C(—CF₂CF₃)—C(=O)—O—(CH₂)₂—SO₂—(CH₂)₂—Rf wherein Rf is a fluoroalkyl group having 1 to 6 carbon atoms.

The alkoxy group-containing monomer (b) is a fluorine-free monomer, and a compound [alkylene glycol (meth)acrylate] of the general formula:

$$CH_2=C(X')—C(=O)—O—(RO)_q—H \qquad (II)$$

wherein X' is a hydrogen atom or a methyl group;
R is an alkylene group having 2 to 4 carbon atoms, in which a part or all of hydrogen atoms may be substituted with hydroxyl groups; and
q is an integer of 1 to 50.

In the alkoxy group-containing monomer (b), preferably, q is 1 to 30, for example, 2 to 10, particularly 2 to 5.

In the general formula (II), R is preferably ethylene or propylene, particularly ethylene. R in the general formulae (II) may be a combination of at least two alkylene. In such case, at least one of R is preferably ethylene. Examples of the combination for R include a combination of ethylene group/propylene group and a combination of ethylene group/butylene group.

The alkoxy group-containing monomer (b) may be a mixture of at least two.

Specific examples of the component (b) include the followings, to which the components (b) is not limited.
CH₂=CHCOO—(CH₂CH₂O)₉—H
CH₂=C(CH₃)COO—(CH₂CH₂O)₉—H
CH₂=C(CH₃)COO—(CH₂CH₂O)₂₃—H
CH₂=C(CH₃)COO—(CH₂CH₂O)₅₀—H
CH₂=C(CH₃)COO—(CH₂CH(CH₃)O)₉—H
CH₂=CHCOO—(CH₂CH(CH₃)O)₉—H
CH₂=C(CH₃)COO—(CH₂CH(CH₃)O)₉—H
CH₂=C(CH₃)COO—(CH₂CH₂O)₅—(CH₂CH(CH₃)O)₂—H
CH₂=C(CH₃)COO—(CH₂CH₂O)₈—(CH₂CH(CH₃)O)₆—H The fluorine-containing copolymer may comprise (c) a crosslinkable monomer. The crosslinkable monomer (c) may be a fluorine-free monomer having at least two reactive groups and/or carbon-carbon double bonds. The crosslinkable monomer (c) may be a compound having at least two carbon-carbon double bonds, or a compound having at least one carbon-carbon double bond and at least one reactive group. Examples of the reactive group include a hydroxyl group, an epoxy group, a chloromethyl group, a blocked isocyanate group and a carboxyl group. In the present invention, a monomer having amino group is not used.

The crosslinkable monomer (c) is preferably a fluorine-free crosslinkable monomer, particularly di(meth)acrylate.

The crosslinkable monomer (c) is preferably a compound (alkylene glycol di(meth)acrylate) of the formula:

$$CH_2=C(X'')—C(=O)—O—(R''O)_q—C(=O)—C(X'')=CH_2 \qquad (III)$$

wherein, each of X'' is a hydrogen atom or a methyl group;
R'' is an alkylene group having 2 to 10 carbon atoms, in which a part or all of hydrogen atoms may be substituted with hydroxyl groups; and
q is an integer of 1 to 50. The number of carbon atoms in R'' is 2 to 10, for example, 2 to 6, particularly 2 to 4. R'' is preferably an ethylene group.

Specific example of alkylene glycol di(meth)acrylate of the formula (III) are as follows:
CH₂=C(CH₃)COO—(CH₂CH₂O)₅—COC(CH₃)=CH₂
CH₂=CHCOO—(CH₂CH₂O)₉—COCH=CH₂
CH₂=C(CH₃)COO—(CH₂CH(CH₃)O)₁₂—COCH=CH₂
CH₂=CHCOO—(CH₂CH₂O)₅—(CH₂CH(CH₃)O)₃—COCH=CH₂
CH₂=C(CH₃)COO—(CH₂CH₂O)₂₃—OOC(CH₃)C=CH₂
CH₂=C(CH₃)COO—(CH₂CH₂O)₂₀—(CH₂CH(CH₃)O)₅—COCH=CH₂

Additional examples of the crosslinkable monomer (c) include diacetoneacrylamide, (meth)acrylamide, N-methylolacrylamide, hydroxymethyl (meth)acrylate, hydroxyethyl (meth)acrylate, 3-chloro-2-hydroxypropyl (meth)acrylate, butadiene, chloroprene, glycidyl(meth)acrylate, 1,6-hexanediol acrylate and neopentylglycol diacrylate, to which the crosslinkable monomer is not limited.

Further examples of the crosslinkable monomer (c) include glycerol (meth)acrylate, acetoacetoxyethyl(meth)acrylate, isocyanate group-containing (meth)acrylates such as 2-isocyanatoethyl methacrylate, and these (meth) acrylates wherein an isocyanate group is blocked with an blocking agent such as methyl ethyl ketoxime.

The crosslinkable monomer (c) may be a mixture of two or more.

The fluorine-containing copolymer may comprise (d) a non-crosslinkable monomer. The non-crosslinkable monomer (d) is a monomer other than the alkoxy group-containing monomer (b), and is generally a fluorine-free monomer. The non-crosslinkable monomer (d) is preferably a fluorine-free monomer having a carbon-carbon double bond. The non-crosslinkable monomer (d) is preferably a vinyl monomer which is free from fluorine. Generally, the non-crosslinkable monomer is a compound having one carbon-carbon double bond.

Examples of the non-crosslinkable monomer (d) include butadiene, chloroprene, maleic acid derivatives, vinyl halide such as the vinyl chloride, ethylene, vinylidene halide such as the vinylidene chloride, vinyl alkyl ether, styrene, alkyl (meth)acrylate and vinyl pyrrolidone, but are not limited to these.

The non-crosslinkable monomer (d) may be a (meth)acrylate ester having an alkyl group. The number of carbon atoms of the alkyl group may be from 1 to 30, for example, from 6 to 30, e.g., from 10 to 30. For example, the non-crosslinkable monomer (d) may be acrylates of the general formula:

$$CH_2=CA^1COOA^2$$

wherein A¹ is a hydrogen atom or a methyl group, and A² is an alkyl group represented by $C_nH_{2n+1}$ (n=1 to 30).

The fluorine-containing copolymer contains 100 parts by weight of the fluorine-containing monomer (a). Preferably, based on 100 parts by weight of the fluorine-containing monomer (a), the amount of the alkoxy group-containing monomer (b) is 10 to 400 parts by weight, for example, 25 to 150 parts by weight, particularly 100 to 43 parts by weight, the amount of the crosslinkable monomer (c) is at most 30 parts by weight, for example, 0.1 to 20 parts by weight, particularly 0.5-10 parts by weight, and the non-crosslinkable monomer (d) is at most 20 parts by weight, for example, 0.1 to 15 parts by weight, particularly 0.5 to 10 parts by weight.

The number-average molecular weight of the copolymer of the present invention may be from 1,000 to 1,000,000, preferably from 5,000 to 500,000. The molecular weight is measured by a gel permeation chromatography in terms of polystyrene.

A polymerization method of producing the copolymer of the present invention is not limited. Various polymerization methods such as a bulk polymerization, a solution polymerization, an emulsion polymerization and a radiation polymerization can be selected. For example, a solution polymerization using an organic solvent and an emulsion polymerization using water or both an organic solvent and water are generally selected. A treatment liquid is produced by diluting a reaction mixture with water or adding an emulsifying agent to make the emulsification in water after the polymerization.

In the present invention, preferably, after the polymerization (for example, the solution polymerization or the emulsion polymerization), a solvent is removed and water is added to disperse the polymer in water.

Examples of the organic solvent include ketones such as acetone and methyl ethyl ketone; esters such as ethyl acetate and methyl acetate; glycols such as propylene glycol, dipropylene glycol monomethyl ether, dipropylene glycol, tripropylene glycol and low molecular weight polyethylene glycol; and alcohols such as ethyl alcohol and isopropanol.

As the emulsifying agent for the emulsion polymerization and for emulsification in water by adding the emulsifying agent after polymerization, various conventional emulsifying agents such as an anionic emulsifying agent, a cationic emulsifying agent and a nonionic emulsifying agent can be used.

As the polymerization initiator, for example, a peroxide, an azo compound or a persulfuric acid-based compound can be used. The polymerization initiator is generally water-soluble and/or oil-soluble.

Specific examples of the oil-soluble polymerization initiator are preferably 2,2'-azobis(2-methylpropionitrile), 2,2'-azobis(2-methylbutyronitrile), 2,2'-azobis(2,4-dimethylvaleronitrile), 2,2'-azobis(2,4-dimethyl-4-methoxyvaleronitrile), 1,1'-azobis(cyclohexane-1-carbonitrile), dimethyl 2,2'-azobis(2-methylpropionate), 2,2'-azobis(2-isobutyronitrile), benzoyl peroxide, di-tertiary-butyl peroxide, lauryl peroxide, cumene hydroperoxide, t-butyl peroxypivalate, diisopropyl peroxydicarbonate, and t-butyl perpivalate.

Specific examples of the water-soluble polymerization initiator are preferably 2,2'-azobisisobutylamidine dihydrochloride, 2,2'-azobis(2-methyl-propionamidine) hydrochloride, 2,2'-azobis[2-(2-imidazolin-2-yl)propane]hydrochloride, 2,2'-azobis[2-(2-imidazolin-2-yl)propane]sulfate hydrate, 2,2'-azobis[2-(5-methyl-2-imidazolin-2-yl)propane]hydrochloride, potassium persulfate, barium persulfate, ammonium persulfate, and hydrogen peroxide.

The polymerization initiator is preferably an organic peroxide wherein a temperature having a half life of ten hours is at least 40° C. The polymerization initiator is particularly preferably t-butyl peroxypivalate.

The polymerization initiator is used in an amount within a range from 0.01 to 5 parts by weight, based on 100 parts by weight of the monomer.

For the purpose of adjusting the molecular weight, a chain transfer agent, for example, a mercapto group-containing compound may be used. Specific examples thereof include 2-mercaptoethanol, thiopropionic acid, and alkyl mercaptan. The mercapto group-containing compound may be used in an amount of at most 10 parts by weight, within a range from 0.01 to 5 parts by weight, based on 100 parts by weight of the monomer.

Specifically, a copolymer can be produced in the following manner.

In a solution polymerization, it is possible to employ a method of dissolving a monomer in an organic solvent, replacing the atmosphere by nitrogen, adding a polymerization initiator and stirring the solution with heating at a temperature within a range from 40° C. to 120° C. for 1 hour to 10 hours. The polymerization initiator generally may be an oil-soluble polymerization initiator.

The organic solvent is inert to the monomer(s) and dissolves the monomer(s), and examples thereof include acetone, chloroform, HCHC225, isopropyl alcohol, pentane, hexane, heptane, octane, cyclohexane, benzene, toluene, xylene, petroleum ether, tetrahydrofuran, 1,4-dioxane, methyl ethyl ketone, methyl isobutyl ketone, ethyl acetate, butyl acetate, 1,1,2,2-tetrachloroethane, 1,1,1-trichloroethane, trichloroethylene, perchloroethylene, tetrachlorodifluoroethane and trichlorotrifluoroethane. The organic solvent may be used in the amount within the range from 50 to 2,000 parts by weight, for example, from 50 to 1,000 parts by weight, based on 100 parts by weight of total of the monomers.

In an emulsion polymerization, there can be used a method of emulsifying monomers in water in the presence of an emulsifying agent, replacing the atmosphere by nitrogen, and polymerizing with stirring, for example, at the temperature within the range from 40° C. to 80° C. for 1 hour to 10 hours. As the polymerization initiator, for example, water-soluble initiators (e.g., benzoyl peroxide, lauroyl peroxide, t-butyl perbenzoate, 1-hydroxycyclohexyl hydroperoxide, 3-carboxypropionyl peroxide, acetyl peroxide, azobisisobutylamidine dihydrochloride, azobisisobutyronitrile, sodium peroxide, potassium persulfate and ammonium persulfate) and oil-soluble initiators (e.g., azobisisobutyronitrile, benzoyl peroxide, di-tert-butyl peroxide, lauryl peroxide, cumene hydroperoxide, t-butyl peroxypivalate and diisopropyl peroxydicarbonate) are used. The polymerization initiator may be used in the amount within the range from 0.01 to 10 parts by weight based on 100 parts by weight of the monomers.

In order to obtain a polymer dispersion in water, which is superior in storage stability, it is desirable that the monomers are emulsified in water by using an emulsifying device capable of applying a strong shearing energy (e.g., a high-pressure homogenizer and an ultrasonic homogenizer) and then polymerized with using the oil-soluble polymerization initiator. As the emulsifying agent, various emulsifying agents such as an anionic emulsifying agent, a cationic emulsifying agent and a nonionic emulsifying agent can be used in the amount within the range from 0.5 to 20 parts by weight based on 100 parts by weight of the monomers. An anionic and/or cationic and/or nonionic emulsifying agent is preferably used. When the monomers are not completely compatibilized, a compatibilizing agent (e.g., a water-soluble organic solvent and a low-molecular weight monomer) capable of sufficiently compatibilizing them is preferably added to these monomers. By the addition of the compatibilizing agent, the emulsifiability and polymerizability can be improved.

Examples of the water-soluble organic solvent include acetone, methyl ethyl ketone, ethyl acetate, propylene glycol, dipropylene glycol monomethyl ether, dipropylene glycol, tripropylene glycol and ethanol. The water-soluble organic solvent may be used in the amount within the range from 1 to 50 parts by weight, e.g., from 10 to 40 parts by weight, based on 100 parts by weight of water. Examples of the low-molecular weight monomer include methyl methacrylate, glycidyl methacrylate and 2,2,2-trifluoroethyl methacrylate. The low-molecular weight monomer may be used in the amount within the range from 1 to 50 parts by weight, e.g., from 10 to 40 parts by weight, based on 100 parts by weight of water.

The treatment agent of the present invention is preferably in the form of a solution, an emulsion or an aerosol. The treatment agent generally comprises the fluorine-containing polymer and a medium (particularly a liquid medium, for example, an organic solvent and/or water). The concentration of the fluorine-containing polymer in the treatment agent may be, for example, from 0.1 to 50% by weight.

The treatment agent of the present invention can be used to treat (for example, surface treat) paper.

The treatment agent of the present invention can be applied to a substrate to be treated by a know procedure. Usually, the treatment agent is diluted or dispersed with an organic solvent or water, is adhered to surfaces of the substrate by a well-known procedure such as an immersion coating, a spray coating and a foam coating, and is dried (surface treatment). For example, the fluorine-containing copolymer may be used so that, in the case of surface treatment, a fluorine atom ratio is 0.01-0.5% by weight, for example, 0.05-0.2% by weight, based on the weight of the paper.

The fluorine-containing copolymer of the present invention bonds well to the substrate, particularly to paper.

The paper can be manufactured by conventional paper manufacturing methods. There can be used an internal addition method wherein the treatment agent is added to pulp slurry before manufacturing the paper, and an external addition method wherein the treatment agent is added to a manufactured paper. Arbitrarily, after a simple drying at room temperature or a high temperature, the use of a heat treatment capable of having the temperature of at most 300° C. (for example, at most 200° C.) depending on the properties of the substrate can exhibit excellent lipophobicity and hydrophobicity.

The present invention can be used for base paper for gypsum board, coating base paper, medium grade paper, ordinary liner and core, pure white neutral roll paper, neutral liner, rust-preventive liner, metal composite paper and kraft paper. The present invention can be used also for neutral printing or writing paper, neutral coating base paper, neutral PPC paper, neutral thermosensible paper, neutral pressure-sensitive paper, neutral ink jet paper, and neutral communication paper.

As a pulp raw material, there may be used any of bleached pulp or unbleached chemical pulp such as kraft pulp or sulfite pulp, bleached or unbleached high yield pulp such as chip pulp, mechanical pulp or thermomechanical pulp, and waste paper pulp of news paper, journals, corrugated board and ink-removed paper. Also, a mixture of the above pulp raw material with synthetic fibers such as asbestos, polyamide, polyimide, polyester, polyolefin or polyvinyl alcohol may be used.

The water resistance of paper can be improved by adding a sizing agent to the paper. Examples of the sizing agent are a cationic sizing agent, an anionic sizing agent, and a rosin-based sizing agent (e.g., acidic rosin-based sizing agent, or neutral rosin-based sizing agent). A styrene-acrylic acid copolymer and an alkylketene dimer are preferred. The amount of the sizing agent may be 0.01 to 5% by weight based on the weight of the pulp.

If needed, the paper may contain additives conventionally used in papermaking, for example, a paper strength-enhancing agent such as starch, modified starch, carboxylmethyl cellulose or polyimide-polyamine-epichlorohydrin resin, a yield-improving agent, a dye, a fluorescent dye, a slime-controlling agent, and a defoaming agent.

If needed, a size press, gate roll coater, bill blade coater, calendar or the like may be used to apply the chemicals (e.g., the treatment agent, starch, polyvinyl alcohol, dye, coating color, or slide-preventive agent) to paper.

In the present invention, an article to be treated is treated with a treatment agent. The "treatment" means that a treatment agent is applied to a substrate by immersion, spraying, coating or the like. The treatment gives the result that the fluorine-containing polymer which is an active component of the treatment agent is penetrated into the internal parts of the substrate and/or adhered to surfaces of the substrate.

The fluorine-containing copolymer of the present invention can form a film as cosmetics. The composition comprising the fluorine-containing copolymer, particularly the composition comprising the fluorine-containing copolymer and water and/or an organic solvent is applied to a human body, particularly to a skin or a nail, and the liquid medium is removed by drying to give a film.

The fluorine-containing copolymer of the present invention can be used for shaping as a mold release agent. The mold release agent is an internal mold release agent or an external mold release agent. For example, the shaping can be made by applying the mold release agent to an inside of a mold, subsequently filing molding materials in the mold, and solidifying the molding materials.

EXAMPLES

Hereinafter, the present invention will be described in more detail by way of Examples. The following Examples are specifically illustrated but are not to be construed to limit the scope of the invention. Throughout Examples, "parts" and "%" are "parts by weight" and "% by weight", unless otherwise specified.

The testing methods used are as follows.
Oil Resistance

The oil resistance of paper is measured according to a procedure extending TAPPI UM-557 (Kit test). One drop of each of test oils indicated in Table 1 is placed on paper, and the penetration state of the oil into the paper is observed 15 seconds later. The maximum of the oil resistance degrees of the test oil which does not penetrate paper is taken as oil resistance.

TABLE 1

| Kit test oil (Oil resistance degree) | Mixing ratio (vol %) | | |
|---|---|---|---|
| | Castor oil | Toluene | Heptane |
| 1 | 100 | 0 | 0 |
| 2 | 90 | 5 | 5 |
| 3 | 80 | 10 | 10 |
| 4 | 70 | 15 | 15 |
| 5 | 60 | 20 | 20 |
| 6 | 50 | 25 | 25 |
| 7 | 40 | 30 | 30 |

TABLE 1-continued

| Kit test oil (Oil resistance degree) | Mixing ratio (vol %) | | |
|---|---|---|---|
| | Castor oil | Toluene | Heptane |
| 8 | 30 | 35 | 35 |
| 9 | 20 | 40 | 40 |
| 10 | 10 | 45 | 45 |
| 11 | 0 | 50 | 50 |
| 12 | 0 | 45 | 55 |

Dispersion Stability in Water

The dispersion stability in water was evaluated as follows:

If it is visually observed that the polymer can disperse uniformly in water, and it is confirmed that there was not clear polymer separation after 24 hours, the evaluation is "Good". Otherwise, the evaluation is "Poor".

Conversion

If the consumption rate of the fluorine-containing monomer in the polymerization is 99.5% or more, relative to the amount of monomer before the start of polymerization, the evaluation is "Good". Otherwise, the evaluation is "Poor".

Copolymers were produced as follows:

Example 1

Into a 100 ml four-necked flask equipped with a reflux condenser, a nitrogen introduction tube, a thermometer and a stirring device, charged were a fluorine-containing monomer: $CH_2=CHC(=O)O-CH_2CH_2C_6F_{13}$ (hereinafter referred to as "C6SFA(a)") (18.6 g), polyethylene glycol acrylate: $CH_2=CHC(=O)O-(CH_2CH_2O)_n-H$ (BLLEMMER AE90, manufactured by NOF Corporation, average of n is 2, hereinafter referred to as "AE90(b)") (11.4 g), 2-mercaptoethanol (0.3 g) and methyl ethyl ketone (hereinafter referred to as "MEK") (45 g). Nitrogen bubbling was done for 30 minutes.

After increase of temperature to 50-65° C. under nitrogen gas stream, PERBUTYL PV (hereinafter referred to as "PV") (0.4 g) was added and the reaction was conducted for 6 hours at 60-65° C.

MEK was removed from the resultant solution at about 70° C. to give a pale yellow polymer residue. Water (122.4 g) was added to the residue, and the internal temperature was kept at about 80° C. for at least 1 hour and cooled to give an aqueous dispersion having a solid content of about 20% by weight.

Example 2

The same polymerization reaction as in Example 1 was repeated except that MEK in Example 1 was replaced by methanol (hereinafter referred to as "MeOH") to give an aqueous dispersion having a solid content of about 20% by weight.

Example 3

The same polymerization reaction as in Example 1 was repeated except that AE90(b) in Example 1 was replaced by polyethylene glycol methacrylate: $CH_2=C(CH_3)C(=O)O-(CH_2CH_2O)_n-H$ (BLLEMMER PE350, manufactured by NOF Corporation, average of n is 8, hereinafter referred to as "PE350 (b)") to give an aqueous dispersion having a solid content of about 20% by weight.

Example 4

Into a 100 ml four-necked flask equipped with a reflux condenser, a nitrogen introduction tube, a thermometer and a stirring device, charged were C6SFA(a) (18.6 g), AE90(b) (5.7 g), polyethylene glycol acrylate: $CH_2=CHC(=O)O-(CH_2CH_2O)_n-H$ (BLEMMER AE200, manufactured by NOF Corporation, average of n is 4.5, hereinafter referred to as "AE200(b)") (5.7 g), 2-mercaptoethanol (0.3 g) and MEK (45 g). The same polymerization reaction as in Example 1 was repeated to give an aqueous dispersion having a solid content of about 20% by weight.

Example 5

Into a 100 ml four-necked flask equipped with a reflux condenser, a nitrogen introduction tube, a thermometer and a stirring device, charged were C6SFA(a) (18.6 g), 2-hydroxyethyl acrylate (hereinafter referred to as "HEA(b)") (3 g), AE200(b) (7.5 g), polyethylene glycol diacrylate: $CH_2=CHC(=O)O-(CH_2CH_2O)_n-C(=O)CH=CH_2$ (BLEMMER ADE300, manufactured by NOF Corporation, average of n is 7, hereinafter referred to as "ADE300(c)") (0.9 g), 2-mercaptoethanol (0.45 g) and MEK (45 g). The same polymerization reaction as in Example 1 was repeated to give an aqueous dispersion having a solid content of about 20% by weight.

Example 6

The same polymerization reaction as in Example 1 was repeated except that HEA(b) in Example 5 was replaced by 2-hydroxyethyl methacrylate (hereinafter referred to as "HEMA(b)") to give an aqueous dispersion having a solid content of about 20% by weight.

Example 7

Into a 100 ml four-necked flask equipped with a reflux condenser, a nitrogen introduction tube, a thermometer and a stirring device, charged were C6SFA(a) (18.6 g), AE200(b) (10.5 g), ADE300(c) (0.9 g), 2-mercaptoethanol (0.45 g) and MEK (45 g). The same polymerization reaction as in Example 1 was repeated to give an aqueous dispersion having a solid content of about 20% by weight.

Example 8

The same polymerization reaction as in Example 1 was repeated except that ADE300(c) in Example 7 was replaced by 2-hydroxy-1-acryloxy-3-methacryloxypropane: $CH_2=CHC(=O)O-CH_2CH(OH)CH_2-O-C(=O)C(CH_3)=CH_2$ (NK Ester 701 A, manufactured by Shin-Nakamura Chemical Co. Ltd., hereinafter referred to as "NK701A (c)") to give an aqueous dispersion having a solid content of about 20% by weight.

Example 9

The same polymerization reaction as in Example 1 was repeated except that ADE300(c) in Example 7 was replaced by 1,6-hexanediol diacrylate: $CH_2=CHC(=O)O-(CH_2)_6-O-C(=O)CH=CH_2$ (NK Ester A-HD, manufactured by Shin-Nakamura Chemical Co. Ltd., hereinafter referred to as "A-HD(c)") to give an aqueous dispersion having a solid content of about 20% by weight.

Example 10

The same polymerization reaction as in Example 1 was repeated except that AE200(b) in Example 5 was replaced by polyethylene glycol methacrylate: $CH_2=C(CH_3)C(=O)O-(CH_2CH_2O)_n-H$ (BLEMMER PE200, manufactured by NOF Corporation, average of n is 4.5, hereinafter referred to as "PE200(b)") to give an aqueous dispersion having a solid content of about 20% by weight.

Example 11

The same polymerization reaction as in Example 1 was repeated except that ADE300(c) in Example 5 was replaced by polyethylene glycol dimethacrylate: $CH_2=C(CH_3)C(=O)O-(CH_2CH_2O)_n-C(=O)C(CH_3)=CH_2$ (NK Ester 4G, manufactured by Shin-Nakamura Chemical Co. Ltd., hereinafter referred to as "NK4G(c)") to give an aqueous dispersion having a solid content of about 20% by weight.

Comparative Example 1

The same polymerization reaction as in Example 1 was repeated except that AE90(b) in Example 1 was replaced by methoxy polyethylene glycol acrylate: $CH_2=CHC(=O)O-(CH_2CH_2O)_n-CH_3$
(NK Ester AM-90G, manufactured by Shin-Nakamura Chemical Co. Ltd., average of n is 9, hereinafter referred to as "AM-90G") to give an aqueous dispersion having a solid content of about 20% by weight.
The finally resultant dispersion in water had poor dispersion stability in water, since a polymer was separated from water after 24 hours.

Comparative Example 2

The same polymerization reaction as in Example 1 was repeated except that AE90(b) in Example 1 was replaced by methoxy triethylene glycol acrylate: $CH_2=CHC(=O)O-(CH_2CH_2O)_n-CH_3$
(Light-Acrylate MTG-A, manufactured by Kyoeisha Chemical Co. Ltd., average of n is 3, hereinafter referred to as "MTG-A") to give an aqueous dispersion having a solid content of about 20% by weight.
The finally resultant dispersion in water was in the separation state between a polymer and water, so that the polymer was not dispersed in water.

Comparative Example 3

The same polymerization reaction as in Example 1 was repeated except that AE90(b) in Example 1 was replaced by methoxy polyethylene glycol methacrylate: $CH_2=C(CH_3)C(=O)O-(CH_2CH_2O)_n-CH_3$
(NK Ester M-90G, manufactured by Shin-Nakamura Chemical Co. Ltd., average of n is 9, hereinafter referred to as "M-90G") to give an aqueous dispersion having a solid content of about 20% by weight.
The finally resultant dispersion in water had poor dispersion stability in water, since a polymer was separated from water after 24 hours.

Comparative Example 4

The same polymerization reaction as in Example 1 was repeated except that AE90(b) in Example 1 was replaced by methoxy diethylene glycol methacrylate: $CH_2=C(CH_3)C(=O)O-(CH_2CH_2O)_n-CH_3$
(NK Ester M-20G, manufactured by Shin-Nakamura Chemical Co. Ltd., average of n is 2, hereinafter referred to as "M-20G"). The conversion of C6SFA(a) was 98.4%.
The finally resultant dispersion in water was in the separation state between a polymer and water, so that the polymer was not dispersed in water.

Comparative Example 5

The same polymerization reaction as in Example 1 was repeated except that AE90(b) in Example 1 was replaced by methoxy polyethylene glycol monomethacrylate: $CH_2=C(CH_3)C(=O)O-(CH_2CH_2O)_n-CH_3$
(BLEMMER PME4000, manufactured by NOF Corporation, average of n is 90, hereinafter referred to as "PME4000") to give an aqueous dispersion having a solid content of about 20% by weight.

Comparative Example 6

The same polymerization reaction as in Example 1 was repeated except that C6SFA(a) in Comparative Example 4 was replaced by C6SFMA(a). The conversion of C6SFMA(a) was 95.0%.
The finally resultant dispersion in water was in the separation state between a polymer and water, so that the polymer was not dispersed in water.

Comparative Example 7

The same polymerization reaction as in Example 1 was repeated except that C6SFA(a) in Example 5 was replaced by C6SFMA(a) and AE200(b) was replaced by MTG-A.
The finally resultant dispersion in water was in the separation state between a polymer and water, so that the polymer was not dispersed in water.

Comparative Example 8

Into a 100 ml four-necked flask equipped with a reflux condenser, a nitrogen introduction tube, a thermometer and a stirring device, charged were C6SFA(a) (18.6 g), AE90(b) (8.4 g), dimethylaminoethyl methacrylate: $CH_2=C(CH_3)C(=O)O-CH_2CH_2N(CH_3)_2$
(Light-Ester DM, manufactured by Kyoeisha Chemical Co. Ltd., hereinafter referred to as "DM") (3 g), 2-mercaptoethanol (0.3 g) and MEK (45 g). Nitrogen bubbling was done for 30 minutes.
After increase of temperature to 50-65° C. under nitrogen gas stream, PERBUTYL PV (hereinafter referred to as "PV") (0.4 g) was added and the reaction was conducted for 6 hours at 60-65° C.

The conversion of C6SFA(a) was 99.2%.

MEK was removed from the resultant solution at about 70° C. to give a pale yellow polymer residue. Water (121.2 g) and acetic acid (1.2 g) were added to the residue, and the internal temperature was kept at about 80° C. for at least 1 hour and cooled to give an aqueous dispersion having a solid content of about 20% by weight.

The finally resultant dispersion in water had poor dispersion stability in water, since a polymer was separated from water after 24 hours.

Comparative Example 9

Into a 100 ml four-necked flask equipped with a reflux condenser, a nitrogen introduction tube, a thermometer and a stirring device, charged were C6SFA(a) (18.6 g), AE200(b) (7.5 g), DM (3 g), 2-mercaptoethanol (0.3 g) and MEK (45 g). The same polymerization reaction as in Comparative Example 8 was conducted.

The finally resultant dispersion in water was in the separation state between a polymer and water, so that the polymer was not dispersed in water.

Comparative Example 10

Into a 100 ml four-necked flask equipped with a reflux condenser, a nitrogen introduction tube, a thermometer and a stirring device, charged were C6SFMA(a) (22.8 g), HEMA (3.3 g), DM (3.6 g) and polyethylene glycol dimethacrylate: $CH_2=C(CH_3)C(=O)O—(CH_2CH_2O)_n—C(=O)C(CH_3)=CH_2$
(NK Ester 3G, manufactured by Shin-Nakamura Chemical Co. Ltd., average of n is 3, hereinafter referred to as "NK3G (c)") (0.3 g) and MEK (45 g). The same polymerization reaction as in Comparative Example 8 was conducted. The conversion of C6SFA(a) was 94.6%.

MEK was removed from the resultant solution at about 70° C. to give a pale yellow polymer residue. Water (121.2 g) and acetic acid (1.2 g) were added to the residue, and the internal temperature was kept at about 80° C. for at least 1 hour and cooled. The finally resultant dispersion in water was in the separation state between a polymer and water, so that the polymer was not dispersed in water.

Comparative Example 11

Into a 100 ml four-necked flask equipped with a reflux condenser, a nitrogen introduction tube, a thermometer and a stirring device, charged were C6SFMA(a) (22.5 g), DM (4.5 g), PE350 (3 g) and MEK (45 g). The same polymerization reaction as in Comparative Example 8 was conducted. The conversion of C6SFMA(a) was 94.7%.

MEK was removed from the resultant solution at about 70° C. to give a pale yellow polymer residue. Water (120.6 g) and acetic acid (1.8 g) were added to the residue, and the internal temperature was kept at about 80° C. for at least 1 hour and cooled to give an aqueous dispersion having a solid content of about 20% by weight.

Test Examples

Production of Test Paper

Test paper was made by using a test paper machine residing in Western Michigan University in USA.

Production method is shown below.

The kind of pulp used was LBKP (broad-leaved tree bleached kraft pulp) and NBKP (narrow-leaved tree bleached kraft pulp) wherein a ratio was 6/4(L/N) and freeness of the used pulp was 400 ml (Canadian Standard Freeness).

Cationized starch, Stayloc 400 (manufactured by Tate and Lyle PLC) in the amount of 2% by weight based on dry pulp was added to a pulp slurry having a pulp content of about 2% by weight. In addition, a sizing agent, Hercon 70 (manufactured by Hercules Corporation) in the amount of 0.0375% by weight based on dry pulp was added to the pulp slurry. The pulp slurry was used to manufacture paper by a Fourdrinier paper machine.

The resultant paper had a basis weight of 60 g/m² and a thickness of 0.1 mm.

External Addition Process

Each of oil-resistant aqueous solutions (in other words, aqueous dispersions of polymer) was diluted with water to a solid content of 0.2% by weight to give a treatment liquid.

After immersing the untreated test paper in the diluted liquid, the paper was squeezed at a squeezing pressure of 0.1 kg/cm by a squeezing machine (a size press method). The wet pickup of the treated test paper was about 90%. The wet pickups are shown in Table 4.

The paper was dried at 115° C. with a drum type dryer for 70 seconds.

Test results are shown in Table 2.

TABLE 1

| | Example No. | | | | | | | | | | |
|---|---|---|---|---|---|---|---|---|---|---|---|
| | 1 | 2 | 3 | 4 | 5 | 6 | 7 | 8 | 9 | 10 | 11 |
| Solvent | MEK | MeOH | MEK | MEK | MEK | MEK | MEK | MEK | MEK | MEK | MEK |
| C6SFA(a) | 62 | 62 | 62 | 62 | 62 | 62 | 62 | 62 | 62 | 62 | 62 |
| HEMA(b) | — | — | — | — | — | 10 | — | — | — | — | — |
| HEA(b) | — | — | — | — | 10 | — | — | — | — | 10 | 10 |
| AE90(b) | 38 | 38 | — | 19 | — | — | — | — | — | — | — |
| AE200(b) | — | — | — | 19 | 25 | 25 | 35 | 35 | 35 | — | 25 |
| PE200(b) | — | — | — | — | — | — | — | — | — | 25 | — |
| PE350(b) | — | — | 38 | — | — | — | — | — | — | — | — |
| ADE300(c) | — | — | — | — | 3 | 3 | 3 | — | — | 3 | — |
| NK4G(c) | — | — | — | — | — | — | — | — | — | — | 3 |
| NK701A(c) | — | — | — | — | — | — | — | 3 | — | — | — |
| A-HD(c) | — | — | — | — | — | — | — | — | 3 | — | — |

TABLE 1-continued

|  | Example No. | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| Kit test (Oil resistance property) | 7 | 8 | 7 | 8 | 8 | 8 | 8 | 7 | 8 | 8 | 8 |
| Dispersion stability in water | Good | Good | Good | Good | Good | Good | Good | Good | Good | Good | Good |
| Conversion | Good | Good | Good | Good | Good | Good | Good | Good | Good | Good | Good |

Notes to Table:
C6SFA(a): $CH_2=CHC(=O)O-CH_2CH_2C_6F_{13}$
HEMA(b): 2-Hydroxyethyl methacrylate
HEA(b): 2-Hydroxyethyl acrylate
AE90(b): Polyethylene glycol acrylate $CH_2=CHC(=O)O-(CH_2CH_2O)_n-H$ (average of n is 2)
AE200(b): Polyethylene glycol acrylate $CH_2=CHC(=O)O-(CH_2CH_2O)_n-H$ (average of n is 4.5)
PE200(b): Polyethylene glycol methacrylate $CH_2=C(CH_3)C(=O)O-(CH_2CH_2O)_n-H$ (average of n is 4.5)
PE350(b): Polyethylene glycol methacrylate $CH_2=C(CH_3)C(=O)O-(CH_2CH_2O)_n-H$ (average of n is 8)
ADE300(c): Polyethylene glycol diacrylate $CH_2=CHC(=O)O-(CH_2CH_2O)_n-C(=O)CH=CH_2$ (average of n is 7)
NK4G(c): Polyethylene glycol dimethacrylate $CH_2=C(CH_3)C(=O)O-(CH_2CH_2O)_n-C(=O)C(CH_3)=CH_2$ (average of n is 4)
NK701A(c): 2-Hydroxy-1-acryloxy-3-methacryloxypropane $CH_2=CHC(=O)O-CH_2CH(OH)CH_2-O-C(=O)C(CH_3)=CH_2$
A-HD(c): 1,6-Hexanediol diacrylate $CH_2=CHC(=O)O-(CH_2)_6-O-C(=O)CH=CH_2$ The results of Comparative Test Examples are shown in Table 3.

TABLE 2

|  | Comparative Example No. | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| Solvnt | MEK | MEK | MEK | MEK | MEK | MEK | MEK | MEK | MEK | MEK | MEK |
| C6SFA(a) | 62 | 62 | 62 | 62 | 62 | — | — | 62 | 62 | — | — |
| C6SFMA(a) | — | — | — | — | — | 62 | 62 | — | — | 76 | 75 |
| HEMA(b) | — | — | — | — | — | — | — | — | — | 11 | — |
| HEA(b) | — | — | — | — | — | — | 10 | — | — | — | — |
| AE90(b) | — | — | — | — | — | — | — | 28 | — | — | — |
| AE200(b) | — | — | — | — | — | — | — | — | 25 | — | — |
| DM | — | — | — | — | — | — | — | 10 | 10 | 12 | 15 |
| PE350(b) | — | — | — | — | — | — | — | — | — | — | 10 |
| AM90G | 38 | — | — | — | — | — | — | — | — | — | — |
| MTG-A | — | 38 | — | — | — | — | 25 | — | — | — | — |
| M90G | — | — | 38 | — | — | — | — | — | — | — | — |
| M20G | — | — | — | 38 | — | 38 | — | — | — | — | — |
| PME4000 | — | — | — | — | 38 | — | — | — | — | — | — |
| ADE300(c) | — | — | — | — | — | — | — | 3 | — | 3 | — |
| NK3G(c) | — | — | — | — | — | — | — | — | — | 1 | — |
| Kit test (Oil resistance property) | 2 | — | 1 | — | 3 | — | — | 6 | — | — | 5 |
| Dispersion stability in water | Poor | Poor | Poor | Poor | Good | Poor | Poor | Poor | Poor | Poor | Good |
| Conversion | Good | Good | Good | Poor | Good | Poor | Good | Poor | Good | Poor | Poor |

Notes to Table:
C6SFA(a): $CH_2=CHC(=O)O-CH_2CH_2C_6F_{13}$
C6SFMA(a): $CH_2=C(CH_3)C(=O)O-CH_2CH_2C_6F_{13}$
HEMA(b): 2-hydroxyethyl methacrylate
HEA(b): 2-Hydroxyethyl acrylate(以下 HEA(b))
AE90(b): Polyethylene glycol acrylate $CH_2=CHC(=O)O-(CH_2CH_2O)_n-H$ (average of n is 2)
AE200(b): Polyethylene glycol acrylate $CH_2=CHC(=O)O-(CH_2CH_2O)_n-H$ (average of n is 4.5)
DM: Dimethylaminoethyl methacrylate $CH_2=C(CH_3)C(=O)O-CH_2CH_2N(CH_3)_2$
PE350(b): Polyethylene glycol methacrylate $CH_2=C(CH_3)C(=O)O-(CH_2CH_2O)_n-H$ (average of n is 8)
AM90G: Methoxypolyethylene glycol acrylate $CH_2=CHC(=O)O-(CH_2CH_2O)_n-CH_3$ (average of n is 9)
MTG-A: Methoxytriethylene glycol acrylate $CH_2=CHC(=O)O-(CH_2CH_2O)_n-CH_3$ (n is 3)
M90G: Methoxypolyethylene glycol methacrylate $CH2=C(CH_3)C(=O)O-(CH_2CH_2O)_n-CH_3$ (average of n is 9)
M20G: Methoxydiethylene glycol methacrylate $CH_2=C(CH_3)C(=O)O-(CH_2CH_2O)_n-CH_3$ (n is 2)
PME4000: Methoxypolyethylene glycol monomethacrylate $CH_2=C(CH_3)C(=O)O-(CH_2CH_2O)_n-CH_3$ (average of n is 90)
ADE300(c): Polyethylene glycol diacrylate $CH_2=CHC(=O)O-(CH_2CH_2O)_n-C(=O)CH=CH_2$ (average of n is 7)
NK3G(c): Polyethylene glycoldi methacrylate $CH_2=C(CH_3)C(=O)O-(CH_2CH_2O)_n-C(=O)C(CH_3)=CH_2$ (n is 3)

TABLE 3

|  | Example No. | | | | | | | | | | | Comparative Ex. No. | | | | |
|---|---|---|---|---|---|---|---|---|---|---|---|---|---|---|---|---|
|  | 1 | 2 | 3 | 4 | 5 | 6 | 7 | 8 | 9 | 10 | 11 | 1 | 3 | 5 | 8 | 11 |
| Solid content of treatment liquid (%) | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| Wet pickup (wt %) | 89 | 90 | 90 | 89 | 90 | 91 | 91 | 89 | 89 | 87 | 91 | 90 | 92 | 93 | 91 | 93 |
| Kit test (Oil resistance) | 7 | 8 | 7 | 8 | 8 | 8 | 8 | 7 | 8 | 8 | 8 | 2 | 1 | 3 | 6 | 5 |
| Dispersion stability in water | Good | Good | Good | Good | Good | Good | Good | Good | Good | Good | Good | Poor | Poor | Good | Poor | Good |
| Conversion | Good | Good | Good | Good | Good | Good | Good | Good | Good | Good | Good | Good | Good | Good | Poor | Poor |

The fluorine-containing polymers of Comparative Examples 2, 4, 6 and 7 were not able to homogeneously disperse in water. Therefore, the external addition process was not performed.

Because the fluorine-containing polymers of Comparative Examples 1, 3 and 5 were able to temporarily disperse in water, paper was treated with these polymers, but enough oil-resistance was not imparted to paper.

Comparative Examples 9 and 10, relating to the fluorine-containing copolymer which contained an amino monomer, were not able to homogeneously disperse. Therefore, the external addition process was not performed.

In Comparative Example 8 having the temporary dispersion in water and in Comparative Example 11 having the homogeneous dispersion in water for 24 hours, paper was treated with the dispersion. The fluorine-containing copolymer of the present invention had better oil-resistance than Comparative Examples 8 and 11.

It is understood that the fluorine-containing copolymer of the present invention can impart equal or more oil resistance in comparison with the fluorine-containing copolymer which contains an amino group.

The invention claimed is:

1. A fluorine-containing polymer free from a monomer having an amino group, comprising (a) a fluorine-containing monomer of the general formula:

$$CH_2=C(-X)-C(=O)-Y-[-(CH_2)_m-Z-]_p-(CH_2)_n-Rf \quad (I)$$

wherein X is a hydrogen atom, a methyl group, a fluorine atom, a chlorine atom, a bromine atom, a iodine atom, a $CFX^1X^2$ group (wherein $X^1$ and $X^2$ is a hydrogen atom, a fluorine atom or a chlorine atom), a cyano group, a linear or branched fluoroalkyl group having 1 to 20 carbon atoms, a substituted or unsubstituted benzyl group, or a substituted or unsubstituted phenyl group;

Y is —O— or —NH—;

Z is —S— or —$SO_2$—;

Rf is a fluoroalkyl group having 1 to 6 carbon atoms;

m is from 1 to 10, n is from 0 to 10, and p is 0 or 1, (b) an alkoxy group-containing monomer of the general formula:

$$CH_2=C(X')-C(=O)-O-(RO)_q-H \quad (II)$$

wherein X' is a hydrogen atom or a methyl group;

R is an alkylene group having 2 to 4 carbon atoms, in which a part or all of hydrogen atoms may be substituted with hydroxyl groups; and q is an integer of 2-50, and (c) a crosslinkable monomer which is di(meth)acrylate of the general formula:

$$CH_2=C(X'')-C(=O)-O-(R''O)_r-C(=O)-C(X'')=CH_2 \quad (III)$$

wherein each of X'' is a hydrogen atom or a methyl group;

R'' is an alkylene group having 2 to 10 carbon atoms, in which a part or all of hydrogen atoms may be substituted with hydroxyl groups; and r is an integer of 1 to 50.

2. The fluorine-containing copolymer according to claim 1, wherein p in the fluorine-containing monomer (a) is an integer of 0.

3. The fluorine-containing copolymer according to claim 1, wherein X in the fluorine-containing monomer (a) is a hydrogen atom.

4. The fluorine-containing copolymer according to claim 1, wherein Rf in the fluorine-containing monomer (a) is a perfluoroalkyl group having 6 carbon atoms.

5. The fluorine-containing copolymer according to claim 1, wherein q in the alkoxy group containing monomer (b) is an integer of 2 to 30.

6. The fluorine-containing copolymer according to claim 1, wherein the alkoxy group-containing monomer (b) is in an amount of 10 to 400 parts by weight, based on 100 amount parts by weight of the fluorine-containing monomer (a), in the fluorine-containing copolymer.

7. The fluorine-containing copolymer according to claim 1, wherein the amount of the crosslinkable monomer (c) is from 0.1 to 30 parts by weight, based on 100 parts by weight of total of the fluorine-containing monomer (a) and the alkoxy group-containing monomer (b).

8. The fluorine-containing copolymer according to claim 1, which is obtained by polymerization using a polymerization initiator which is an organic peroxide wherein a temperature having a half life of ten hours is at least 40° C.

9. The fluorine-containing copolymer according to claim 8, wherein the polymerization initiator is t-butyl peroxypivalate.

10. The fluorine-containing copolymer according to claim 1, wherein the number-average molecular weight of the fluorine-containing copolymer is from 1,000 to 1,000,000.

* * * * *